United States Patent [19]

Schnabel et al.

[11] Patent Number: 4,863,609

[45] Date of Patent: Sep. 5, 1989

[54] PROCESS FOR THE FRACTIONAL SEPARATION OF PROTEIN MIXTURES BY MEANS OF MEMBRANES

[75] Inventors: Roland Schnabel, Hofheim; Hans V. Baeyer, Berlin, both of Fed. Rep. of Germany

[73] Assignee: Schott Glaswerke, Fed. Rep. of Germany

[21] Appl. No.: 552,814

[22] Filed: Nov. 17, 1983

[30] Foreign Application Priority Data

Dec. 9, 1982 [DE] Fed. Rep. of Germany ....... 3245591

[51] Int. Cl.$^4$ .............................................. B01D 13/00
[52] U.S. Cl. .................................. 210/641; 210/651; 210/500.26
[58] Field of Search ..................... 210/651, 321.3, 411, 210/641, 500.26, 195.2

[56] References Cited

U.S. PATENT DOCUMENTS

| | | | |
|---|---|---|---|
| 3,148,141 | 9/1964 | Schonenberger et al. | 210/651 X |
| 3,228,877 | 1/1966 | Mahon | 210/321.3 X |
| 4,404,102 | 9/1983 | Pradel et al. | 210/411 X |
| 4,478,719 | 10/1984 | Michele et al. | 210/641 |

OTHER PUBLICATIONS

International Publication #WO82/03568, 10-1982.

Primary Examiner—Frank Spear
Attorney, Agent, or Firm—Wegner & Bretschneider

[57] ABSTRACT

Protein mixtures are separated by utilizing membrane filtration. Filtration rates of at least 60%, preferably at least 70%, can be achieved when the liquid protein mixture to be separated is diluted at least tenfold, preferably twentyfold.

12 Claims, 4 Drawing Sheets

PROCESS FOR THE FRACTIONAL SEPARATION OF PROTEIN MIXTURES BY MEANS OF MEMBRANES

BACKGROUND OF THE INVENTION

Various processes for separating mixtures of different substances are used in industrial processing, engineering, biotechnology and medicinal technology to purify, concentrate, and recover specific substances. Examples of such processes are those well-known methods, extraction, distillation, freeze-drying, precipitation and chromatographic separation. In medicinal technology, hematology in particular, centrifugal processes have been utilized for separating solid blood ingredients from plasma; such processes, generally called plasmapheresis, were developed in 1959 J. L. Tullis; D. M. Surgenor; R. J. Tinch; M. D'Hont "New Principle of closed system centrifugation", Science 24, 792, (1956). In the past ten years, plasmaphersis has been supplemented in medicinal technology as well as in biotechnology by membrane separation techniques. Membrane separation provides a less disruptive process for the separation of suspended particles which often are very sensitive. In medicinal technology the process is called membrane plasmapheresis and in chemistry and biotechnology it is called cross-flow-microfiltration. A. S. Michaelis; Desalination 35, 329, (1980).

Although plasmapheresis represents a significant advance in the art and the concentration of certain classes of substances by ultrafiltration or hemofiltration is known, R. Schnabel; Fette-Seifen-Anstrichmittel 81 Nr. 2, 83 (1979), it has been difficult until now to achieve both a fractional and a selective separation of mixtures of certain substances. The question of selectivity is of vital importance because of so-called concentration polarization effects, by formation of secondary membranes and by interactions between the membrane and the substances being separated, the separation threshold expected because of the pore size is shifted H. Chmiel; Therapeutic Plasma Exchange; Ed. H. J. Gurland, v. Heinze, H. A. Lee; Springer, 15, (1981).

The above reference lists 560 citations relating to medicinal plasmapheresis. The separation of components of different molecular weights by cascade filtration, fractional membrane plasmapheresis, and specific membrane plasmapheresis, is discussed. cf. H. Strathmann; Chemie Technik 11 Nr. 7, 813, (1982). By connecting microfiltration membranes, ultrafiltration membranes and hyperfiltration membranes in series, it is possible to separate macromolecular substances from lower molecular weight substances.

Porous glass capillary membranes suitable for such filtration processes are described in German PS No. 2 454 111, and the use of those materials for the diafiltration of blood is described in German PS No. 2 757 673. Use of a combination of different membranes in the arrangement described is described by H. G. Sieberth in "Plasma Exchange Symposiomband," Ed. H. G. Sieberth, Schattauer Verlag 29, (1980). However, the arrangement described there in the form tested was indicated as not being practical. It is less than satisfactory in several important respects. First the membranes in vivo showed a totally different behavior as compared to the values measured in vitro. Second, albumin recovery was too low so that albumin had to be replaced and electrolyte solution (the filtrate) had to be added to the plasma in order to keep up its protein concentration constant. J. Takeda; Y. Ono; K. Yagita; Y. Sume; K. Katoka; Artificial Organs, Vo. 5 (Suppl.) 168, (1981 denominate this replacement a dilution. However, the dilution is only a three folt dilution at most.

The inadequate recovery of low molecular substances at membranes, which per se are technologically optimized, is due to the fact that filtration rates of up to 40 percent are used. If these substances are retained by the membrane or by the secondary layer which builds up on the membrane, only low recovery rates can be achieved.

SUMMARY OF THE INVENTION

It is an object of the present invention to provide an improved a process for the separation of protein mixtures, such as blood, milk, fermentation liquors, etc. by means of membranes. Another object of the invention is to provide a process suitable for operation in a continuous manner to achieve recovery rates of the low molecular substances of more than 60 percent, while at the same time separating completely the macromolecular substances present in the liquid mixture.

Surprisingly, it has been found that filtration rates of more than 70 percent can be achieved if the liquid mixture to be separated is diluted least tenfold and preferably twentyfold. At such dilutions, essentially no secondary membrane is built up and the separation thresholds (cut-off characteristics) of the membranes obtained in vitro with single species solutions are essentially unchanged. The dilution solution is also used for back washing the membrane so that a behavior of the membrane is achieved which is essentially constant with respect to time. This is particularly advantageous in fractional membrane plasmapheresis. The high filtration capability of plasma separation membranes leads to the result that more than 60 percent of the human proteins may be recirculated and no foreign protein need be added.

DETAILED DESCRIPTION

The overall process of the invention is described in the examples which follow. It is within the scope of the invention that the individual process steps can be used separately for special applications. The invention is further illustrated in FIG. 1, which schematically shows the process including the material balance. The designation ff in FIG. 1 stands for filtration fraction, which is a measure of the percentage of separated solution with respect to the amount of solution used. The process comprises the following steps:

I. Separation of corpuscular, colloidally dissolved or suspended ingredients (preceding stage);

II. Tenfold dilution of the solution obtained in stage I;

III. Concentration of the macromolecular ingredients or separation of the dilution medium together with the low molecular ingredients at filtration rates higher than 70 percent; and IV. Concentration of the ingredients to be returned or separation of the dilution medium containing electrolytes or molecules down to a size smaller than the substances to be returned to stage I.

According to a further aspect of the invention, additional stages can be incorporated after stage IV in order to achieve a further fractionation of the mixture being separated.

The membrane design of filters to be used depends on the size of the molecular species to be separated. The pore sizes of the membranes decrease in sequence, larger to smaller, in the path of flow. Proper pore size selection is essential for optimum separation to be achieved.

Figure 1:
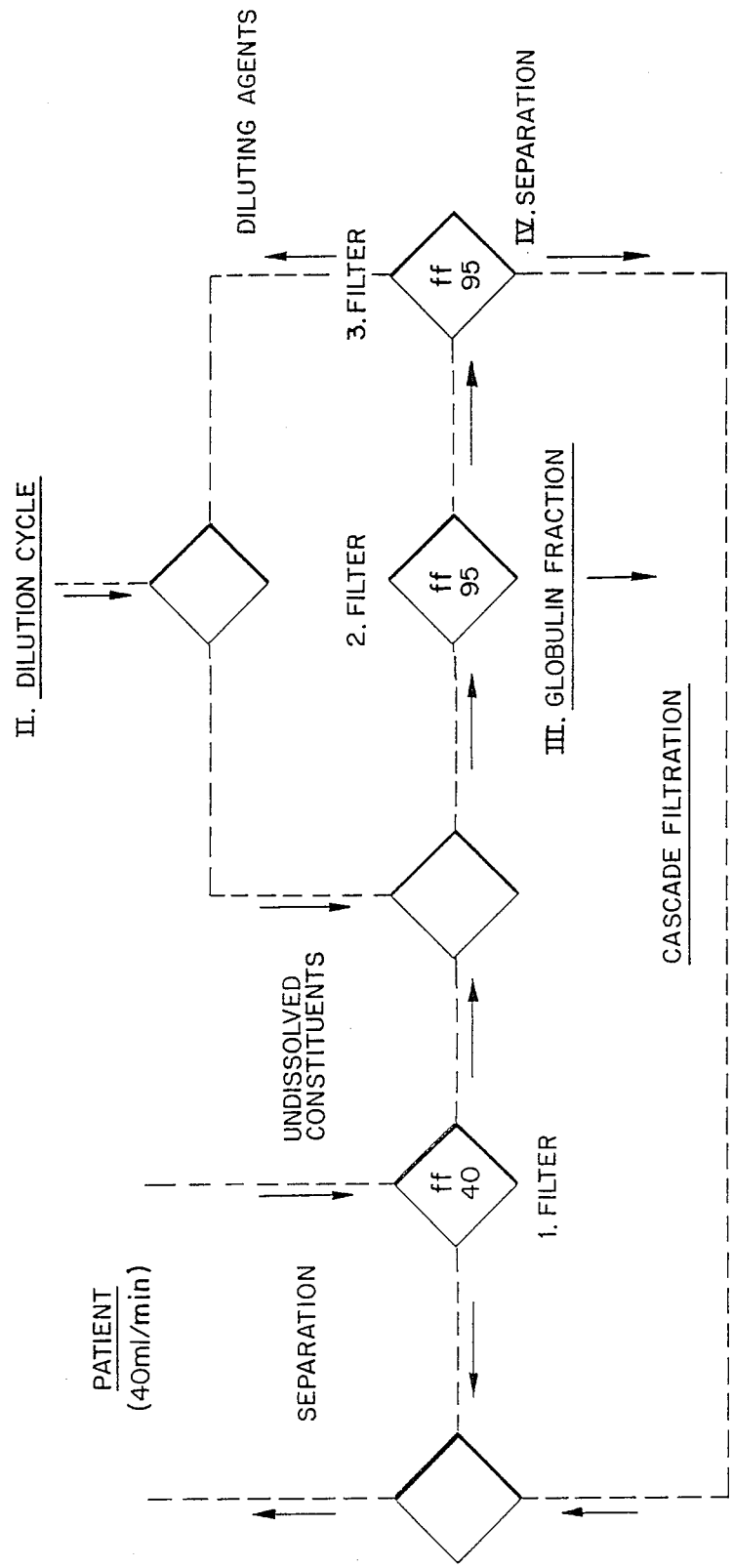
FIG. 1 is a schematic representation of a blood separation process according to the present invention.

FIG. 1 illustrates membrane cascade plasmapheresis of blood. During treatment, blood is taken from the patient at the rate of 40 ml/min. This rate of blood withdrawal shown here is only an example; it can be higher or lower.

Normally, blood consists of about 40 percent corpuscular ingredients and of about 60 percent blood plasma. About 40 percent of the total volume of the plasma, after having been diluted 1:20, passes from the first filter (plasma separator) to the second filter. In the second filter, the high molecular portion is concentrated at constant volume and at filtration rates of 95 percent. That portion contains all ingredients above the separation threshold (cut-off characteristics) according to the threshold determined by the membrane pore size. In the example shown, this includes molecules above 150,000 molecular weight (this fraction is called the globulin fraction). Depending on the nature of the patient's disease, this fraction can either be discarded or can be further separated by renewed dilution and separation. The ultrafiltrate of stage III is passed to a further membrane which in this particular case is a hemofiltration membrane. In this stage IV separation, the molecular weight portion above 60,000 is concentrated at constant volume and at a high filtration rate while the ultrafiltrate is returned to the dilution cycle. The fraction between 60,000 and 150,000 daltons, which contains human albumin and a large part of the coagulation factors, is returned to the patient together with the concentrate of stage I.

The material balance of the example shows that the process is working at constant volume, and that no foreign substances are returned to the patient with the exception of a small portion of electrolyte solution. Under the conditions chosen for this example, which can be varied, treatment of from 2-3 hours is sufficient to filter 6-7 liters of blood.

During the course of the fractionation, constant volume is achieved by adding pre-determined amounts of liquid and removing predetermined quantities of filtrate. Pressure within the system increases because of increasing membrane resistance, and as soon as a predetermined maximum pressure is obtained—in the example illustrated this is 500 torr—a back-washing step is is performed with the diluting medium. Accordingly, the operating pressure returns to its initial value.

The following examples further illustrate the process without limiting the scope of the invention. The examples have been performed with glass membranes which are particularly useful. However, membranes made of other material such as plastic may also be used.

EXAMPLE 1

Figure 2:
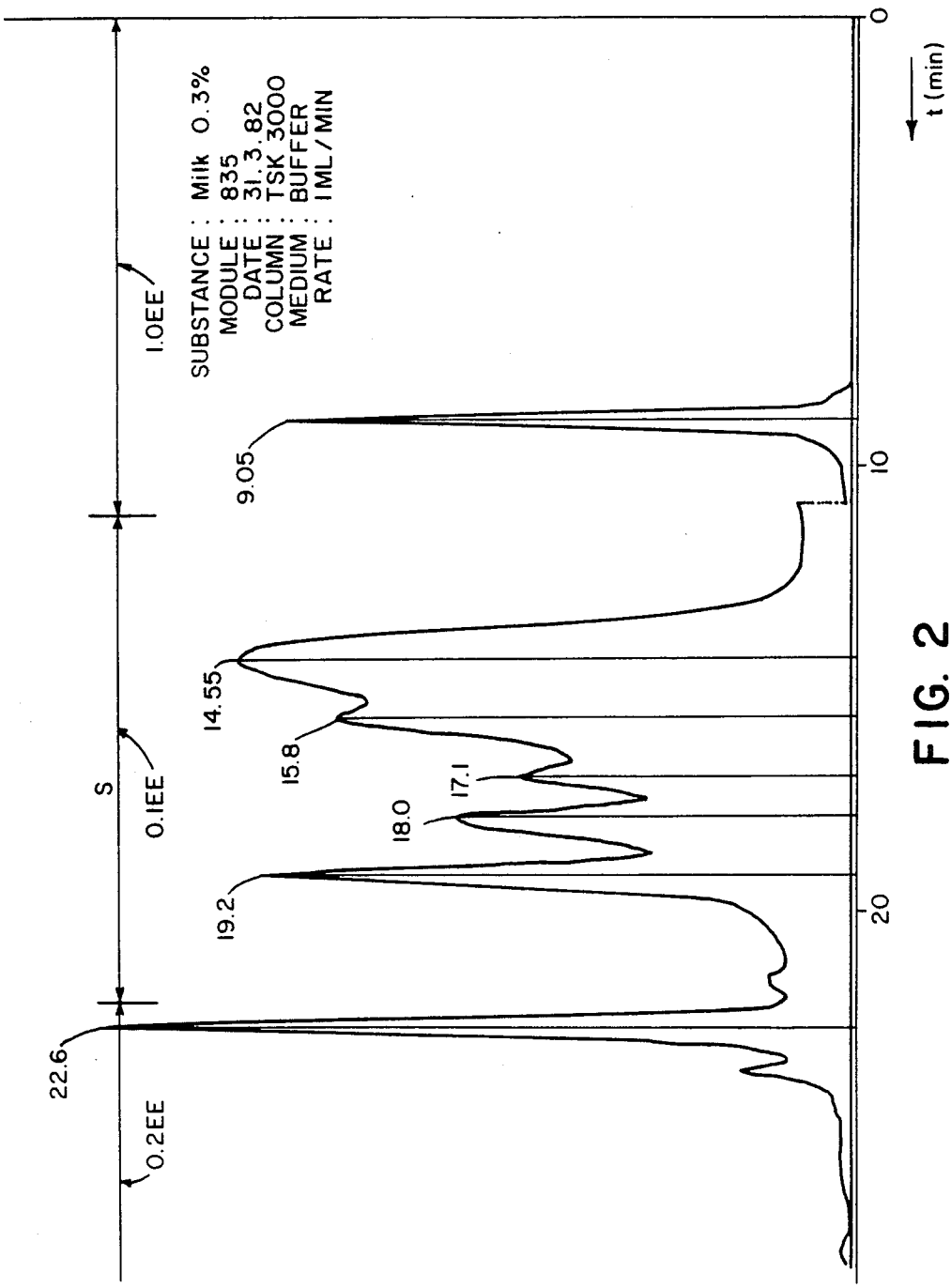
FIGS. 2-4 are HPLC-chromatograms resulting from various phases of the process in Example 1 below.
Figure 3:
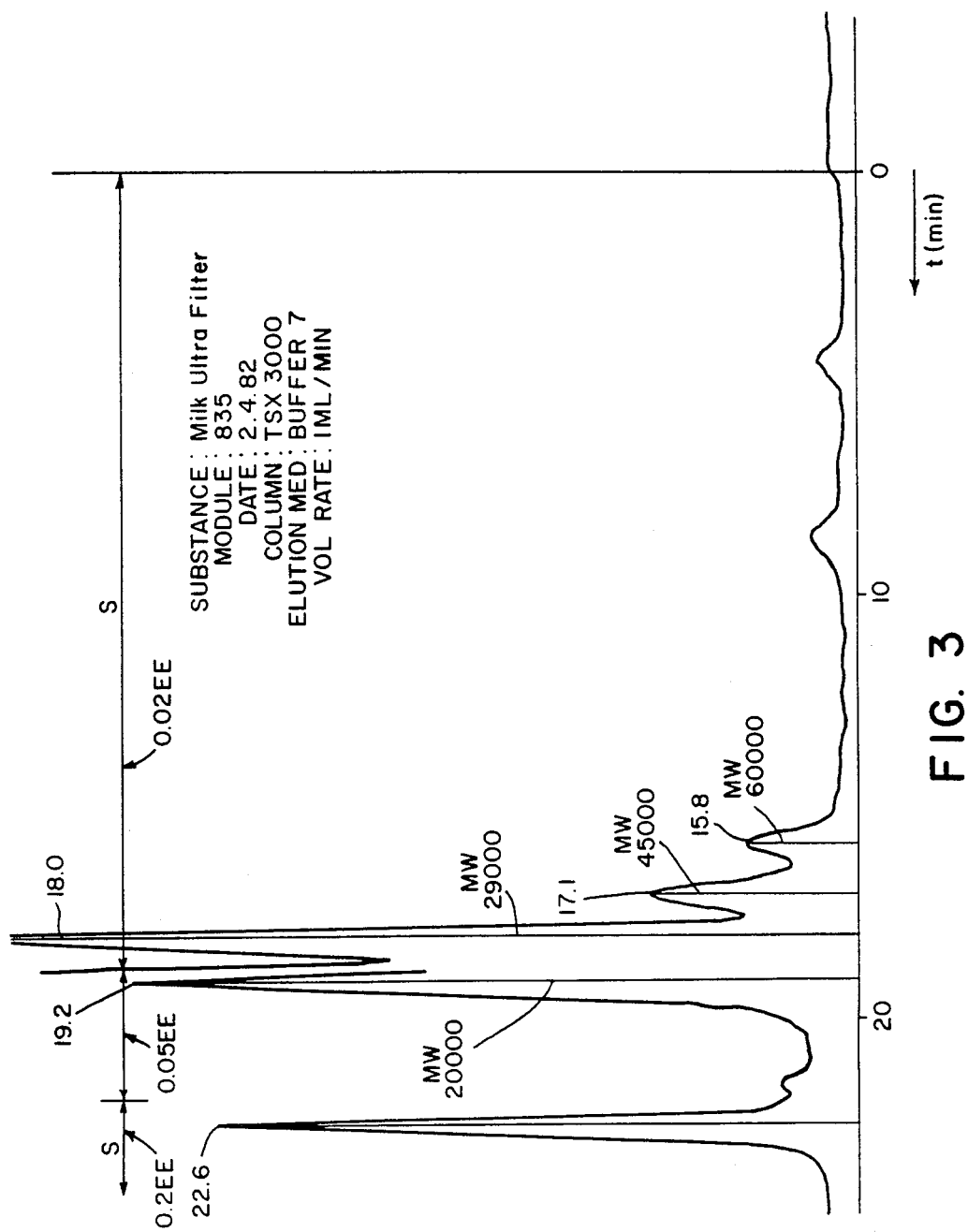

Defatted milk containing 0.3 percent fat was separated into different ingredients. A filter was used, the capillary membranes of which had a wall thickness of 57 $\mu$m and an internal diameter of 282 $\mu$m. The pore volume of the membrane was 0.6 ml/g, and the average pore radius was 12.4 nm. The treated milk had a composition which is shown in the HPLC-chromatogram of FIG. 2. After the colloidal and higher molecular ingredients (68 000 Daltons) had been separated, the distribution shown in FIG. 3 was obtained. The results are as follows:

Passage mw 68,000:6.8%
45,000:18.8%
29,000:53.5%
20,000:71.4%

Figure 4:
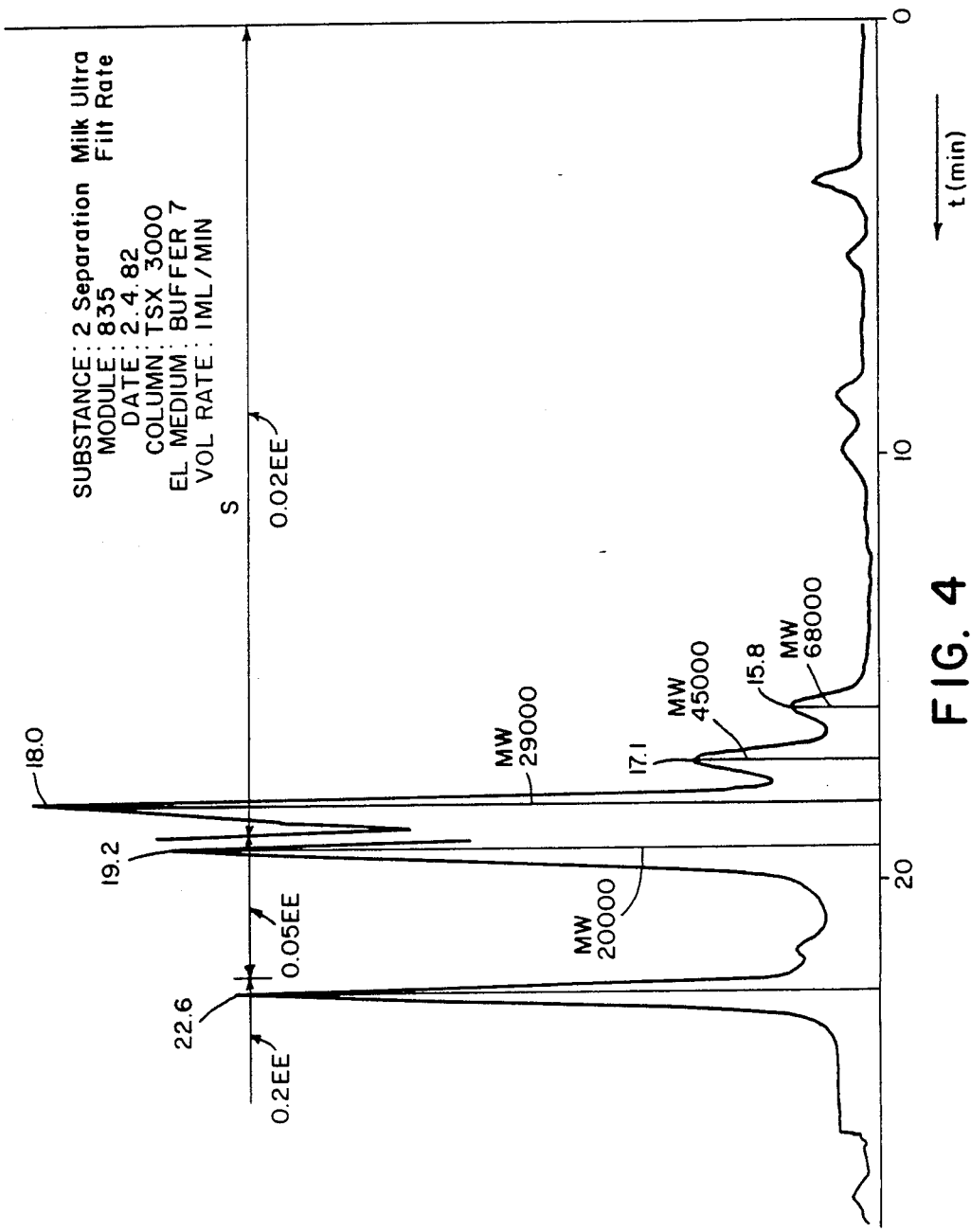

The permeate used in the concentration stage had the following values as shown in FIG. 4:
Passage mw 68,000:79.2%
45,000:85.4%
24,000:93.5%
20,000:94.7%

It is note worthy that all separation steps were performed with a single kind of membrane. The difference in the separation effect was achieved only by the different concentration of the substances concerned.

EXAMPLE 2

Blood from a patient with dermatomysites was fractionated. After the corpuscular ingredients had been separated, and at a dilution rate of 1:20 (which is illustrated by stage II of the process scheme shown in FIG. 1), the diluted plasma was transferred to stage III for further separation, and was then concentrated in stage IV.

The following distribution was obtained, based on the individual substances:

| Substance | charged [mg/min] | recovered [mg/min] | yield [%] |
|---|---|---|---|
| albumin | 66.94 | 45.12 | 67.4 |
| immunoglobulin G | 8.45 | 5.21 | 62 |
| immunoglobulin A | 1.17 | 0.46 | 39 |
| immunoglobulin M | 1.17 | * | 0 |

*too small to measure

EXAMPLE 3

Blood of a patient with IGA plasmocytoma was treated according to Example 2. The dilution rate was 1:14.

| Substance | charged [mg/min] | recovered [mg/min] | yield [%] |
|---|---|---|---|
| $\alpha_1$ Antitrypsin | 1.78 | 1.08 | 61 |
| albumin | 21.12 | 12.67 | 60 |
| transferrin | 1.48 | 0.38 | 26 |
| immunoglobulin G | 1.42 | 0.75 | 53 |
| immunoglobulin A | 32.99 | 12.47 | 38 |
| caeruloplasimin | 0.15 | * | 0 |
| complement C$_4$ | 0.17 | 0.05 | 29 |
| complement C$_3$ | 0.43 | 0.14 | 33 |
| immunoglobulin M | 0.13 | * | 0 |

*too small to measure

The reduction of immunoglobulin A by 62% at a albumin recovery rate of 60%, calculated over the total time of treatment, clearly demonstrates the advantages of the process of the invention over prior art process.

The process of the present invention is applicable to the separation of protein mixtures of all kinds. It may be used for the processing of fermentation broths where the final product is to be separated from the enzyme, from other high molecular substances and from corpuscular ingredients. For example a separation system according to the process may be connected directly to an enzyme reactor.

What is claimed is:

1. A process for fractional separation of protein mixtures by means of membranes; comprising:

removing a protein mixture to be separated from a starting vessel;

diluting the protein mixture to be separated at least tenfold with a dilution medium;

introducing the diluted mixture into a first membrane filtration stage wherein high molecular weight substances are separated at a filtration rate of at least 70 percent; and passing the filtrate of said first membrane filtration stage to a second membrane filtration stage to separate said filtrate at a filtration rate of at least 70 percent into low molecular weight substances and said dilution medium said dilution medium being recycled to said diluting step and said low molecular weight substances being recycled to said starting vessel.

2. A process according to claim 1, wherein the dilution is a twenty-fold dilution.

3. A process according to claim 1, wherein a preceding stage is interposed before said diluting step in which the separation of undissolved ingredients is made at a filtration rate of at most 60 percent without any dilution of the mixture.

4. The process according to claim 3, wherein the protein mixture is a fermentation liquor.

5. A process according to claim 3, wherein the membranes are glass membranes.

6. A process according to claim 3, wherein the process is used to carry out fractional membrane plasmaphoresis.

7. A process according to claim 1, wherein the dilution medium is back washed through the membrane at predetermined intervals with respect to time or to the amount of the dilution medium separated.

8. A process according to claim 7, wherein the stagewise separation and back-wash are performed in a pressure-controlled manner.

9. A process according to claim 7, wherein the stagewise separation and back-wash are performed in a volume-controlled manner.

10. The process according to claim 1, wherein the protein mixture is a fermentation liquor.

11. A process according to claim 1, wherein the membranes are glass membranes.

12. A process according to claim 1, wherein the process is used to carry out fractional membrane plasmaphoresis.

* * * * *